US009168155B2

(12) United States Patent
Earl et al.

(10) Patent No.: US 9,168,155 B2
(45) Date of Patent: Oct. 27, 2015

(54) MODULAR FEMORAL PROVISIONAL

(75) Inventors: Brian D. Earl, South Bend, IN (US);
Marvin Figueroa, Warsaw, IN (US);
Travis H. Campbell, Warsaw, IN (US)

(73) Assignee: Zimmer, Inc., Warsaw, IN (US)

(*) Notice: Subject to any disclaimer, the term of this patent is extended or adjusted under 35 U.S.C. 154(b) by 1332 days.

(21) Appl. No.: 11/680,711

(22) Filed: Mar. 1, 2007

(65) Prior Publication Data
US 2008/0215157 A1   Sep. 4, 2008

(51) Int. Cl.
A61F 2/38     (2006.01)
A61F 2/46     (2006.01)
A61F 2/30     (2006.01)
A61F 2/28     (2006.01)

(52) U.S. Cl.
CPC ............ *A61F 2/4684* (2013.01); *A61F 2/3859* (2013.01); *A61F 2002/2825* (2013.01); *A61F 2002/305* (2013.01); *A61F 2002/30316* (2013.01); *A61F 2002/30331* (2013.01); *A61F 2002/30352* (2013.01); *A61F 2002/30383* (2013.01); *A61F 2002/30604* (2013.01); *A61F 2002/30607* (2013.01); *A61F 2002/30616* (2013.01); *A61F 2002/30672* (2013.01); *A61F 2002/30878* (2013.01); *A61F 2220/0025* (2013.01)

(58) Field of Classification Search
CPC .............................................. A61F 2002/3863
See application file for complete search history.

(56) References Cited

U.S. PATENT DOCUMENTS

| | | | | | |
|---|---|---|---|---|---|
| 4,714,474 | A | * | 12/1987 | Brooks et al. | 623/20.33 |
| 5,645,602 | A | * | 7/1997 | Albrektsson et al. | 623/23.11 |
| 5,782,925 | A | * | 7/1998 | Collazo et al. | 623/20.28 |
| 2003/0225458 | A1* | | 12/2003 | Donkers et al. | 623/20.15 |
| 2005/0177169 | A1* | | 8/2005 | Fisher et al. | 606/88 |
| 2005/0278034 | A1* | | 12/2005 | Johnson et al. | 623/20.15 |
| 2007/0233266 | A1* | | 10/2007 | Williams et al. | 623/20.14 |
| 2008/0004701 | A1* | | 1/2008 | Axelson et al. | 623/16.11 |
| 2008/0221569 | A1* | | 9/2008 | Moore et al. | 606/53 |

FOREIGN PATENT DOCUMENTS

| | | | | | |
|---|---|---|---|---|---|
| FR | 2851156 A1 | * | 8/2004 | | A61F 2/38 |
| WO | WO9730661 | * | 8/1997 | | A61F 2/30 |

OTHER PUBLICATIONS

Machine translation or FR 2851156 A1. 8 Pages. Accessed on Sep. 2, 2014.*

* cited by examiner

*Primary Examiner* — Thomas J Sweet
*Assistant Examiner* — Rebecca Preston
(74) *Attorney, Agent, or Firm* — Schwegman Lundberg & Woessner, P.A.

(57) ABSTRACT

A provisional prosthetic system that replicates the characteristics of a corresponding, nonprovisional femoral prosthesis. The provisional prosthetic system may include a frame component and a shell component. The frame component of the provisional prosthetic system may be configured to be attached directly to a resected femur. In one exemplary embodiment, the frame component is impacted onto the resected femur to firmly seat therewith. Once the frame component is secured to the resected femur, a shell component of the provisional prosthetic system may be positioned on and secured to the frame component. In one exemplary embodiment, the frame component is made from a metallic material. This allows for the frame component to maintain the rigidity necessary to facilitate proper trialing. In another exemplary embodiment, the shell component is a plastic.

6 Claims, 6 Drawing Sheets

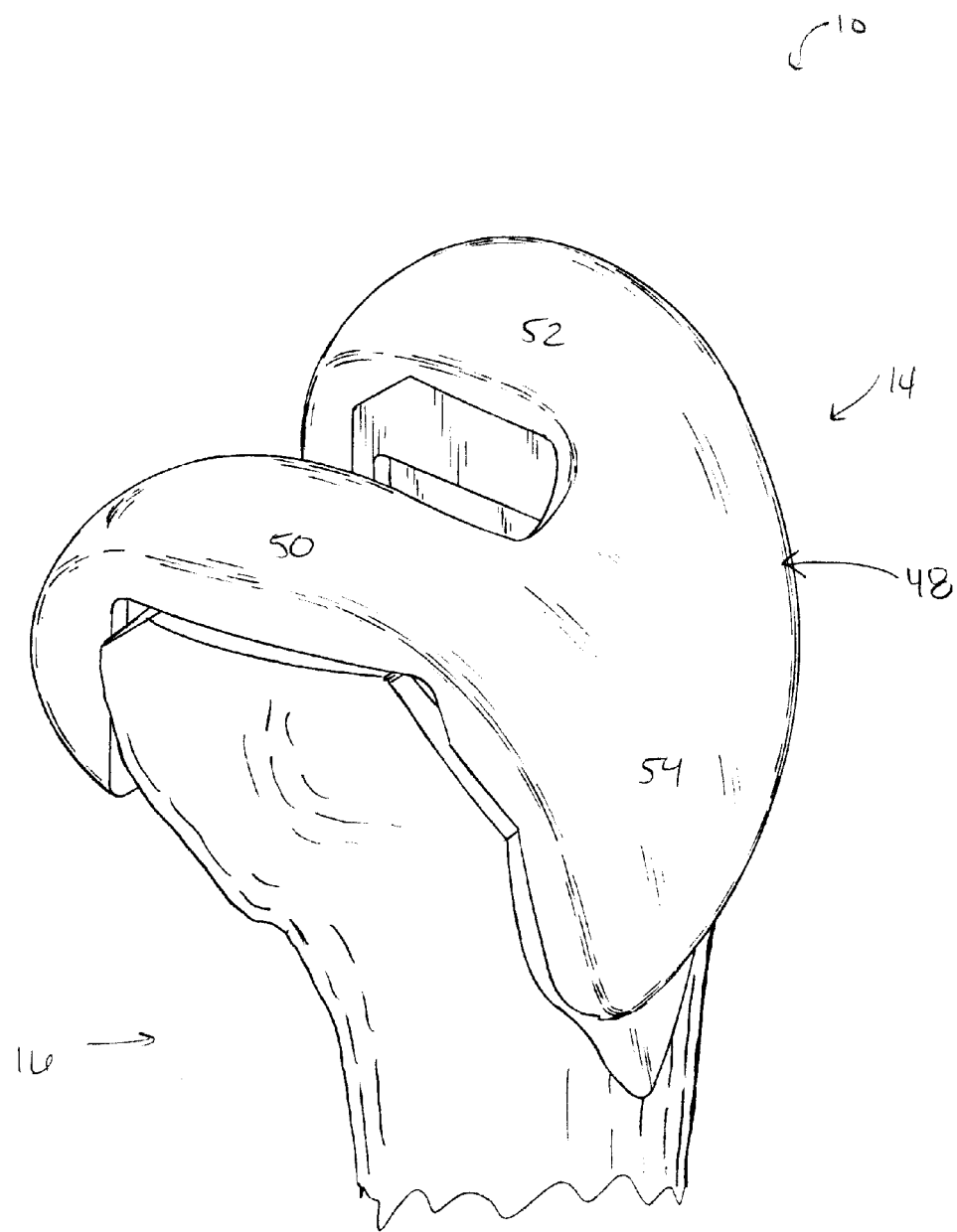
FIG_7

MODULAR FEMORAL PROVISIONAL

BACKGROUND

1. Field of the Invention

The present invention relates to a provisional prosthetic system and the surgical methods for utilizing the same.

2. Description of the Related Art

Prostheses are commonly utilized to repair and/or replace damaged bone and tissue in the human body. For example, a knee prosthesis may be implanted to replace damaged or destroyed bone in the tibia and/or femur and to recreate the natural, anatomical articulation of the knee joint. To implant a prosthesis, orthopedic surgery is performed which requires the creation of an incision in the skin of the patient and may necessitate the retraction of surrounding tissue to provide the surgeon with access to the surgical site.

To facilitate the implantation of a prosthesis, modular prostheses may be utilized. Modular prostheses have several individual, distinct components which are connected together to form the final, implanted prosthesis. For example, a modular knee prosthesis may include individual femoral, tibial, and patellar components which are connected together to form the final, implanted knee prosthesis. Additionally, one component, e.g., a femoral implant in a modular knee prosthesis system, may be selected from several different femoral components having various configurations, all of which are included in the modular prosthesis system. By selecting the femoral component that best accommodates an individual patient's anatomy, the surgeon may assemble a prosthesis that more closely approximates the natural anatomy of the patient.

In addition to the final, implanted components of a modular prosthesis system, a modular prosthesis system may also include provisional components which replicate the size and shape of the final, implanted components of the modular prosthesis system. The use of provisional components provides the surgeon with the ability to test the ultimate configuration of the prosthesis prior to the implantation of the final components. By trialing, i.e., testing, the surgeon is able to determine whether the fit, alignment, and range of motion provided by the final prosthesis will approximate the patient's natural anatomy. Additionally, as many implants achieve some measure of press fit with the resected bone, it is important that the provisional components maintain similar stiffness to the implant so that implant fit to bone can be checked prior to implantation. To ensure that the provisional components accurately replicate the function of the final, implanted components, the provisional components are dimensionally equivalent to the implanted components and are frequently manufactured from the same material.

SUMMARY

The present invention relates to a provisional prosthetic system and the surgical methods for utilizing the same. In one embodiment, the provisional prosthetic system replicates the characteristics of corresponding, nonprovisional femoral prostheses. In this embodiment, the provisional prosthetic system includes a frame component and a shell component. The frame component of the provisional prosthetic system may be configured to be attached directly to a resected femur. In one exemplary embodiment, the frame component is impacted onto the resected femur to firmly seat therewith. Once the frame component is secured to the resected femur, the shell component of the provisional prosthetic system may be positioned on and secured to the frame component. In one exemplary embodiment, the frame component is made from a metallic material. This allows for the frame component to maintain the rigidity necessary to facilitate proper trialing. In another exemplary embodiment, the shell component is a plastic. In yet another exemplary embodiment, the shell component is fabricated by injection molding.

To ensure that a provisional and, ultimately, a nonprovisional that has the characteristics most suited for an individual patient are selected, the provisional prosthetic system may include a plurality of shell components having different characteristics, e.g., different sizes, orientations, and/or designs that correspond to available nonprovisional prostheses. For example, if the prosthesis includes three different nonprovisional implants having different sizes, three provisional implants would be included in the prosthesis system which correspond in size to the three nonprovisional implants. Thus, a surgeon may attach a first shell component to the frame component of the provisional prosthetic system and trial, i.e., test, the same. If the surgeon is not satisfied with the results of the current shell component, the surgeon may remove the shell component from the frame component and attach a different shell component having different characteristics, until the best fit for an individual patient is identified.

By utilizing the provisional prosthetic system of the present invention, numerous benefits are realized. For example, by utilizing the frame component and shell component design of the present system, only a single frame component is attached to the resected femur. Thus, the need to impact and remove various provisional components from the resected bone is eliminated and wear of the natural bone stock during the trialing of the provisional components is lessened. Additionally, by eliminating the need to manufacture the shell components of the provisional prosthetic system from a metallic material, the weight of the full complement of provisional components is substantially lessened. This decreases the burden on operating room personnel and hospital staff to stock, inventory, clean, and transport the full complement of provisional components. Moreover, by manufacturing the shell components of the present provisional system from plastic, for example, the cost of producing the same is decreased.

Further, because a plurality of different shell components may be attached to a single frame component, the total number of provisional components in any given provisional system may be decreased. For example, in an implant system having femoral components for standard size, plus size, and minus size for each of the left knee and the right knee, a single frame component may be designed to accept all six configurations of the corresponding shell components. Thus, a single frame can be combined with the differing shell components to form provisional components that accurately replicate the characteristics of the six corresponding nonprovisional implants.

By providing a full complement of provisional components having a mass and volume substantially less than that of a complement of standard provisional components, a hospital may be more likely to stock the entire system. Additionally, a surgeon may request the entire complement of components in the operating room and thus the surgeon may be able to achieve better extension and flexion gap balancing, without the need to perform additional bone cuts or to extensively test the flexion and extension gaps.

In one form thereof, the present invention provides a modular provisional system, including a frame component configured to be secured to the distal end of a femur; and a shell component configured to be releaseably secured to the frame component, the frame component and the shell component cooperating to form a provisional implant which replicates the characteristics of at least one nonprovisional component of a prosthesis system.

In another form thereof, the present invention provides a modular provisional system, including a frame component having first engagement structure, the frame component configured for securement to the distal end of a femur; and a shell component having a frame contacting surface and an articulation surface, at least a portion of the frame contacting surface configured to engage the first engagement structure of the frame component to secure the shell to the frame, the articulation surface of the shell component shaped to replicate natural femoral condyles, wherein the frame component and the shell component cooperate to replicate a characteristic of at least one nonprovisional component of a prosthesis system.

In another form, thereof the present invention provides a method of trialing a femoral implant including the steps of attaching a frame component to the distal end of a femur; attaching a shell component having an articulation surface to the frame component, wherein the frame component and the shell component cooperate to form a first provisional implant; trialing the first provisional implant formed by the frame component and the shell component.

BRIEF DESCRIPTION OF THE DRAWINGS

The above-mentioned and other features and advantages of this invention, and the manner of attaining them, will become more apparent and the invention itself will be better understood by reference to the following description of an embodiment of the invention taken in conjunction with the accompanying drawings, wherein:

FIG. 7 is an assembled view of the provisional prosthetic system of FIG. 1.

Corresponding reference characters indicate corresponding parts throughout the several views. The exemplifications set out herein illustrates preferred embodiments of the invention and such exemplifications are not to be construed as limiting the scope of the invention any manner.

DETAILED DESCRIPTION

Figure 1:
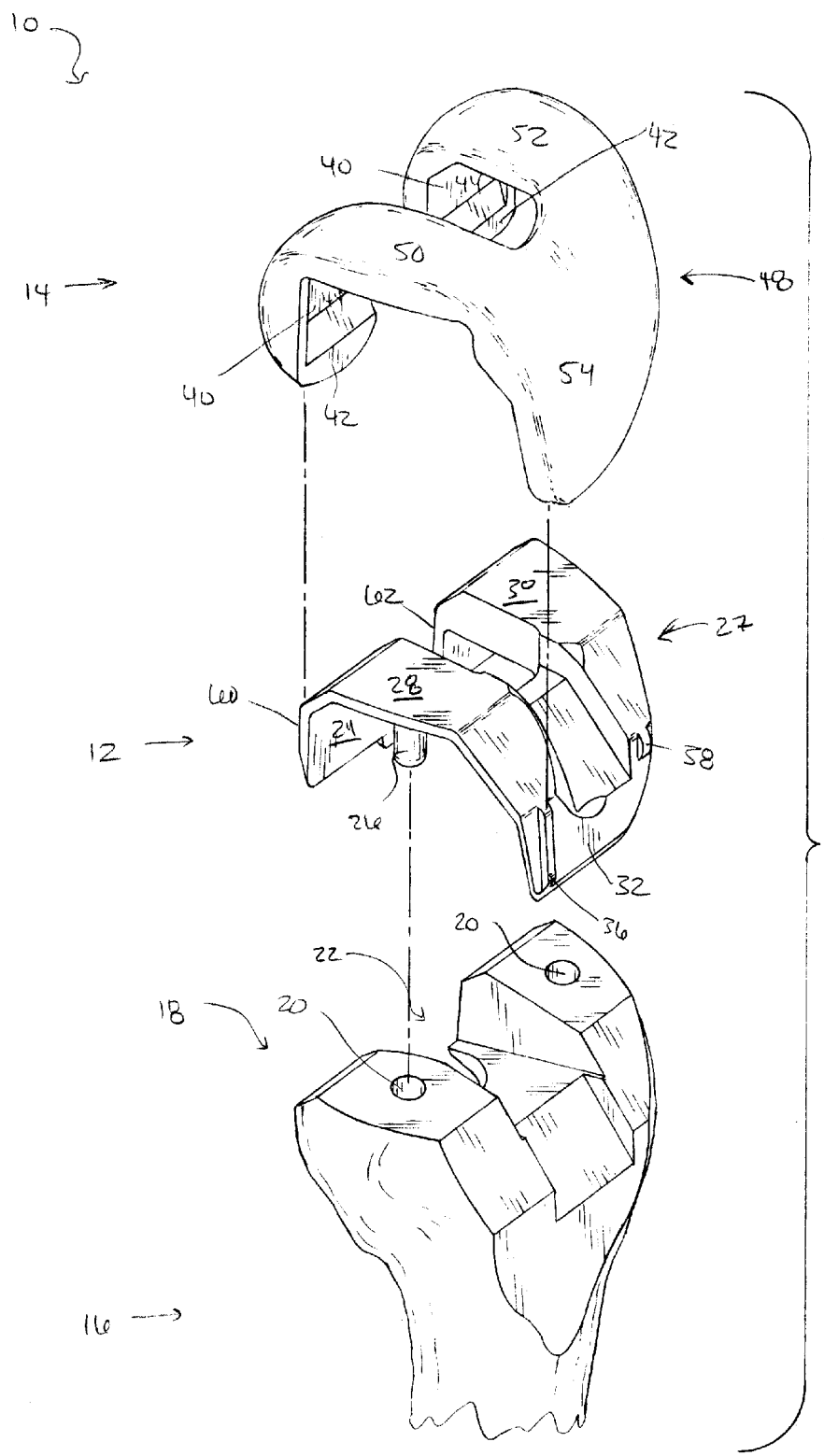
FIG. 1 is an exploded perspective view of one embodiment of the provisional prosthetic system and depicting a resected femur.
Figure 2:
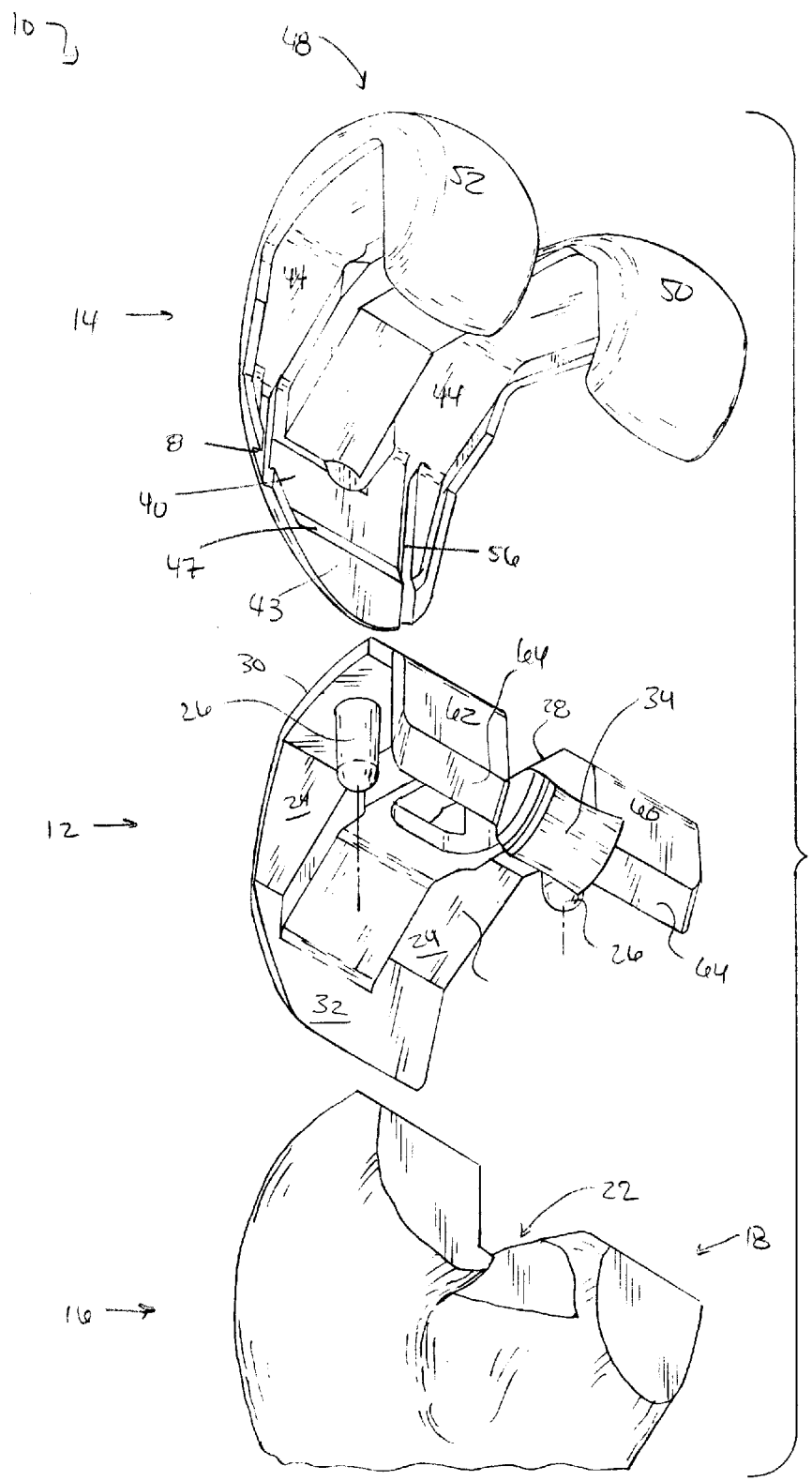
FIG. 2 is another perspective view of the embodiment of FIG. 1, taken from a posterior aspect.
Figure 3:
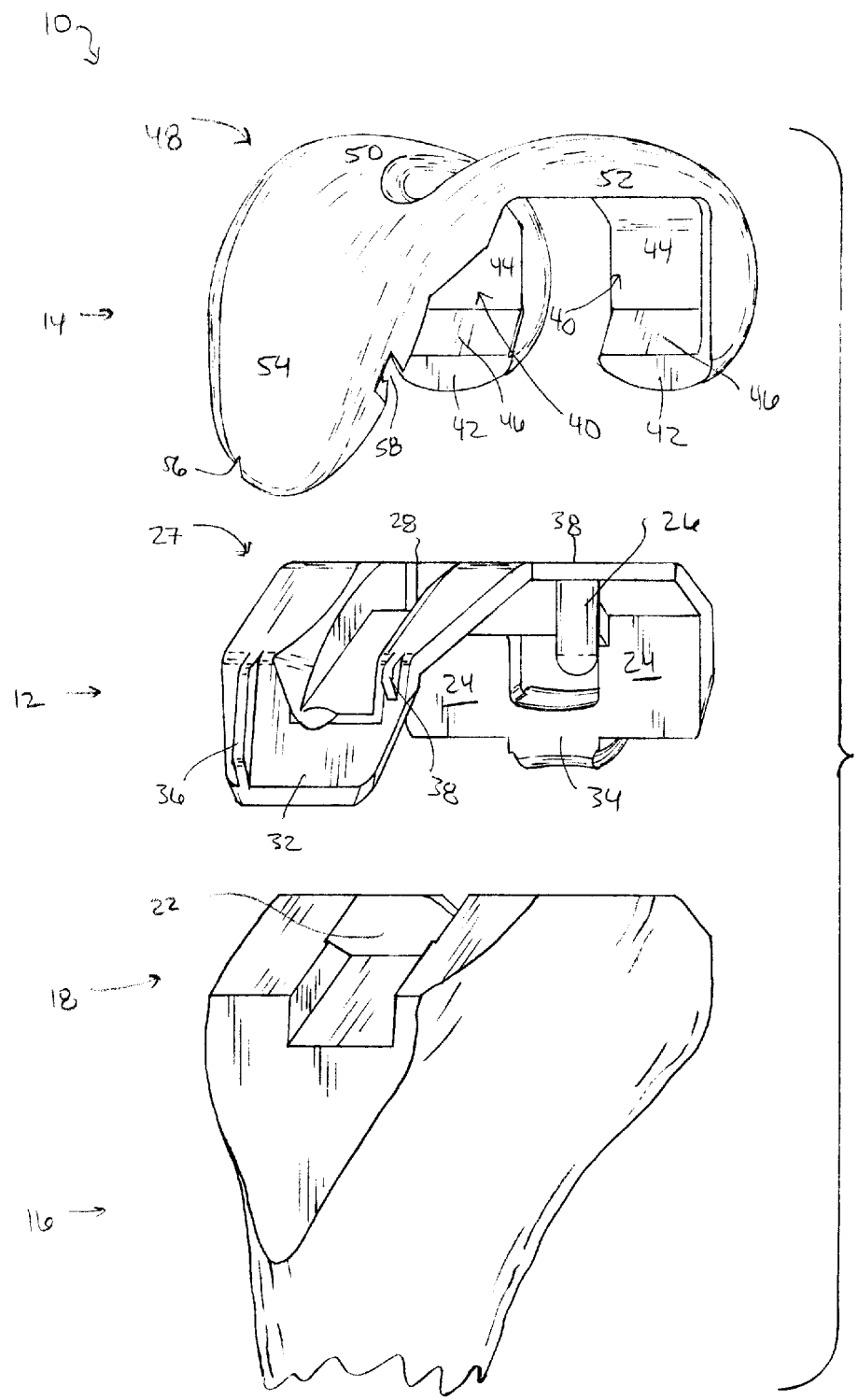
FIG. 3 is another perspective view of the embodiment of FIG. 1 taken from a medial aspect.

As shown in FIGS. 1-3, femoral provisional 10 includes frame component 12 and shell component 14. Shell component 14 may be attached to frame component 12, as shown in FIG. 7, to form assembled femoral provisional 10, as described in detail below. Referring to FIGS. 1-3, frame component 12 of femoral provisional 10 is configured for direct attachment to femur 16. As shown in FIG. 1, femur 16 includes resected distal end 18 having apertures 20 and cutout 22 formed therein. Resected distal end 18 of femur 16 is fully resected, i.e., all of the cuts necessary for implantation of a final, nonprovisional femoral component have been made. In another exemplary embodiment, resected distal end 18 may include only a portion of the cuts necessary to facilitate implantation of the final, nonprovisional femur component. In this embodiment, femoral provisional 10 may be utilized to facilitate a surgeon's determination of the location for making the remaining cuts to femur 16.

In one exemplary embodiment, frame component 12 is formed from a metallic material, e.g., formed from a metal, a metal alloy, or a material having properties that are substantially similar to a metal or metal alloy. This provides frame component 12 with the necessary rigidity to represent the rigidity of the corresponding nonprovisional component on the resected bone and retain shell component 14 in the proper position during trialing. Frame component 12 of femoral provisional 10 includes bone contacting surface 24 and posts 26, best seen in FIG. 2. Bone contacting surface 24 of frame component 12 is shaped to mate with resected distal end 18 of femur 16 and posts 26 are sized to be received within apertures 20. Apertures 20 of femur 16 may be formed by drilling, reaming, or any other known technique. Apertures 20 are sized slightly larger than posts 26, but are close enough in size to posts 26 that frame component 12 may be impacted to be properly seated on distal end 18 of femur 16. While frame component 12 is described and depicted herein as including posts 26, posts 26 are not necessary to the function of frame component 12 and further embodiments are envisioned in which posts 26 are absent.

Frame component 12 further includes shell contacting surface 27 having condylar bases 28, 30 connected by anterior bridge portion 32 and posterior bridge portion 34 (FIG. 3). In one exemplary embodiment, posterior bridge portion 34 replicates the cam of a Posterior Stabilized femoral implant. In another exemplary embodiment configured for a Posterior Cruciate Ligament Retaining femoral prosthesis, posterior bridge portion 34 is absent. Additionally, ribs 36, 38 extend from shell contacting surface 27 of frame component 12 to add rigidity and facilitate retention and alignment of shell component 14 upon frame component 12, as discussed in detail below.

Referring to shell component 14, shell component 14 includes posterior overhang 42, anterior overhang 43 (FIG. 2), and frame contacting surface 40 forming condylar recesses 44. Condylar recesses 44 are separated from overhangs 42, 43 by tapered leads 46, 47, respectively, which facilitate attachment of shell component 14 to frame component 12. In one exemplary embodiment, shell component 14 is formed from a plastic. For example, shell component 14 may be formed from an injection molded polymer. By forming shell component 14 from a plastic or other polymer, the weight of shell component 14 and, correspondingly, femoral provisional 10 is significantly reduced. Thus, a full complement of provisional components made in accordance with the present invention is significantly lighter than a full complement of standard provisional components, lessening the burden on operating room personnel and hospital staff who must transport the same.

Shell component 14 also includes articulating surface 48 having condylar portions 50, 52 connected by anterior portion 54. Referring to FIG. 2, shell component 14 further includes grooves 56, 58 extending through frame contacting surface 40 and overhang 43. Grooves 56, 58 are configured to receive and retain ribs 36, 38 of frame component 12, respectively, therein. Additionally, both grooves 56, 58 include an indentation (not shown) configured to matingly engage ribs 36, 38, respectively. Thus, receipt of ribs 36, 38 within the indentations of grooves 56, 58 provide for retention of anterior portion 54 of shell component 14 upon anterior bridge portion 32 of frame component 12. In one exemplary embodiment, the engagement of ribs 36, 38 with grooves 56, 58 forms a snap-fit connection. Moreover, ribs 36, 38 and grooves 56, 58 facilitate the alignment and seating of shell component 14 with frame component 12 prior to attachment.

Referring to FIGS. 1-3, condylar recesses 44 (FIGS. 1 and 2) of shell component 14 are configured to receive portions of condyle bases 28, 30 of frame component 12 therein. Specifically, condylar recesses 44 and tapered lead 46 are configured to engage posterior portions 60, 62 and tapered edge 64 (FIG. 2), respectively. Thus, posterior portions 60, 62 and condylar bases 28, 30 of frame component 12 are in posterior mating engagement with condylar recesses 44 and tapered lead 46 of shell component 14. In one exemplary embodiment, the interaction of condylar recesses 44, tapered lead 46, posterior portions 60, 62 and tapered edge 64 forms a snap-fit connection. To remove shell component 14 from frame component 12, a surgeon simply lifts up on anterior portion 54 of shell component 14, for example, to release the snap-fit connection. Shell component 14 may then be replaced by another shell component 14 having different characteristics.

Figure 6:
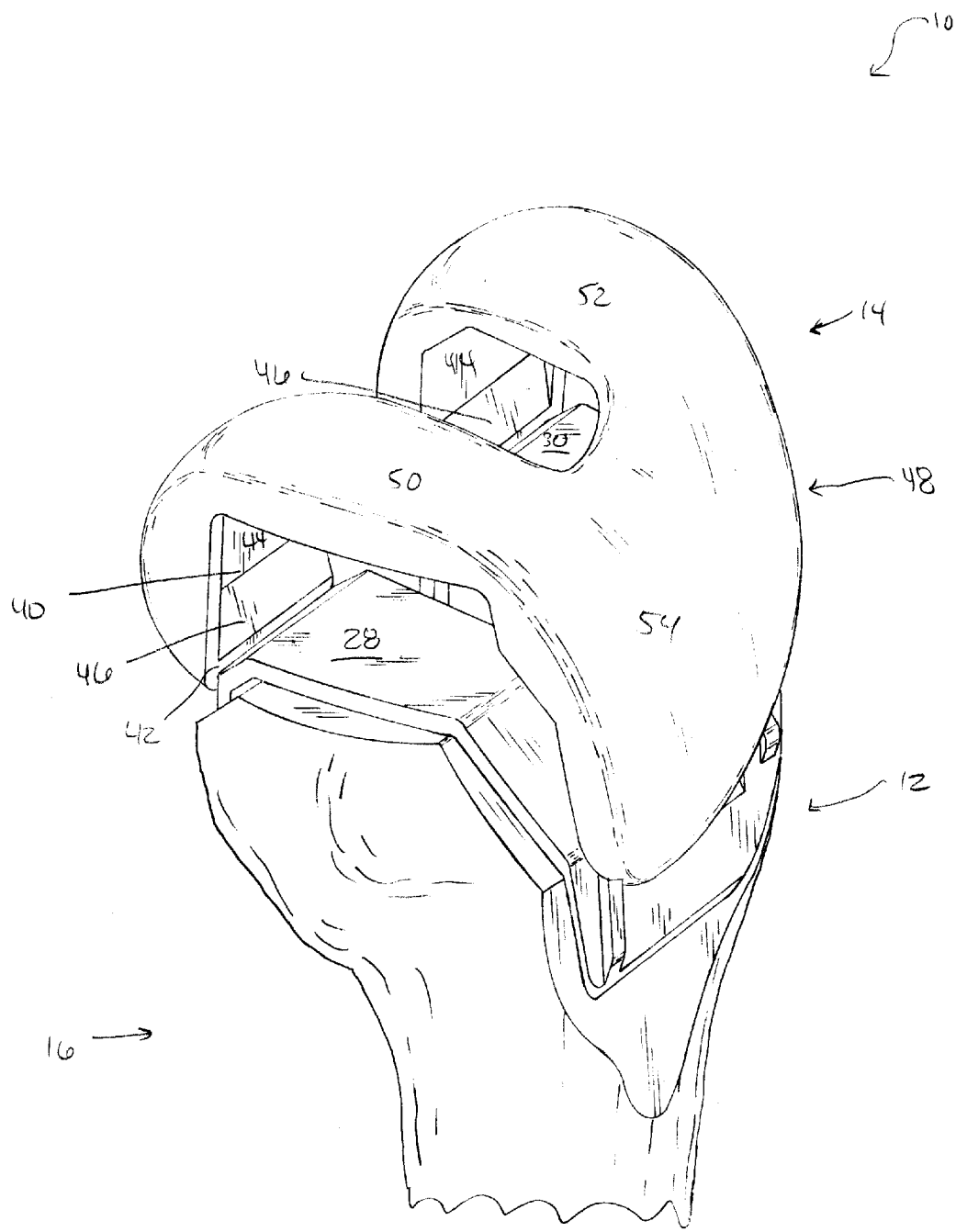
FIG. 6 is a partial assembled view of the provisional prosthetic system of FIG. 1.

To assemble femoral provisional 10 upon femur 16, femur 16 is initially resected, as described above, to form resected distal end 18. Apertures 20 are then formed in resected distal end 18 of femur 16 and sized to receive post 26 of frame component 12 therein. In one exemplary embodiment, frame component 12 is selected from a plurality of frame components having different characteristics. With post 26 aligned with apertures 20, frame component 12 is impacted onto resected distal end 18 of femur 16 until bone contacting surface 24 is in mating engagement with resected distal end 18, as shown in FIG. 6. Referring to FIGS. 6 and 7, once frame component 12 is securely seated on femur 16, one of a plurality of shell components 14 having characteristics which a surgeon believes would best accommodate a patient's natural anatomy is aligned with and secured to frame component 12, as described in detail above. Alternatively, one of a plurality of shell components 14 may be secured to frame component 12 prior to seating frame component 12 on femur 16. Thus, once frame and shell components, 12, 14 are secured together, the assembly is impacted on femur 16 as described above. With shell component 14 secured to frame component 12 and, correspondingly, femur 16, a surgeon may perform trialing of femoral provisional 10.

In the event the surgeon determines that femoral provisional 10 satisfactorily replicates the patient's natural anatomical movement, shell component 14 may be removed from frame component 12 and frame component 12 removed from femur 16. A nonprovisional femoral component having characteristics which correspond to femoral provisional 10 is then implanted using standard surgical techniques.

In the event a surgeon determines femoral provisional 10 does not satisfactorily replicate a patient's natural anatomical movement, shell component 14 may be removed from frame component 12, which provides the sole securement of shell component 14 to femur 16 as described in detail above, and a different shell component 14 having different characteristics may be attached to the same frame component 12. By using a single frame component 12 capable of attachment to multiple shell components 14, the need to impact and remove various frame components 12 is eliminated. Thus, wear of resected distal end 18 of femur 16 is lessened. Additionally, by providing for attachment of multiple shell components 14 to a single frame component 12, the total number of components is lessened. The surgeon may then trial the new femoral provisional 10. Once a surgeon has identified the one of a plurality of shell components 14 that would satisfactorily replicate the patient's natural anatomical movement, femoral provisional 10 may be removed from femur 16, as described in detail above, and the corresponding nonprovisional femoral component implanted.

Figure 4:
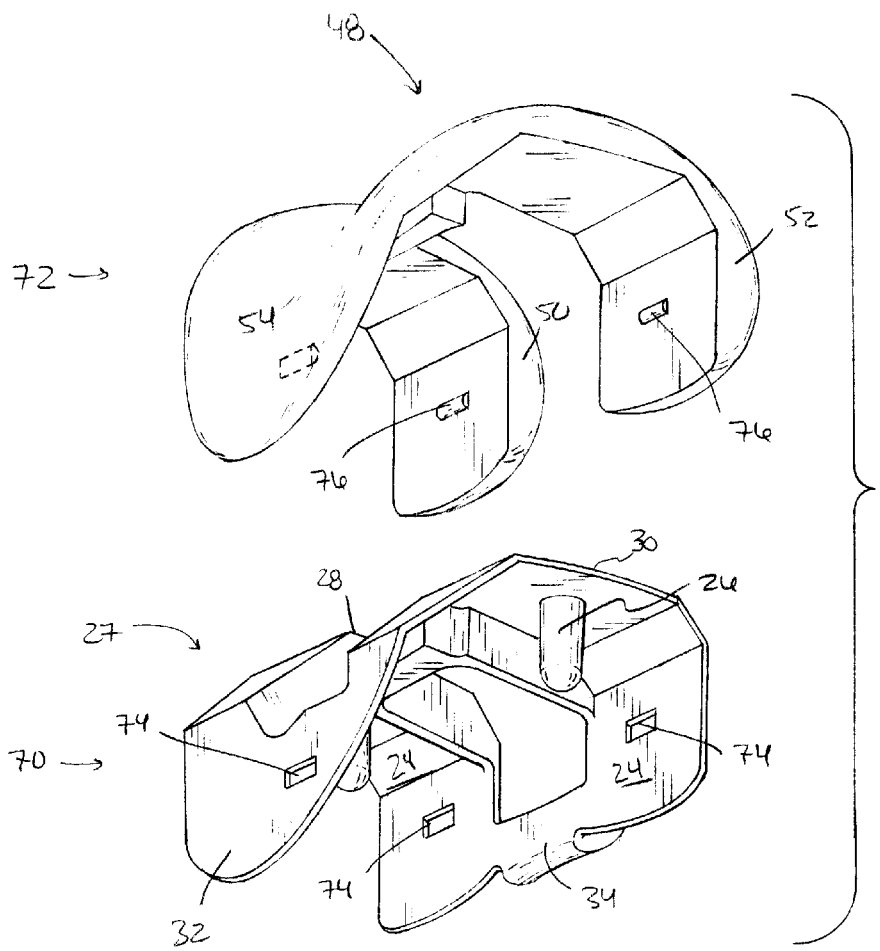
FIG. 4 is an exploded perspective view of the provisional prosthetic system according to another exemplary embodiment.
Figure 5:
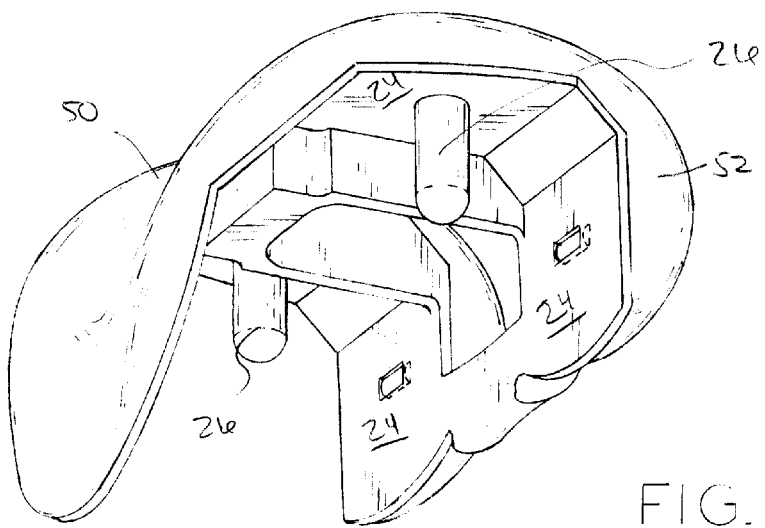
FIG. 5 is an assembled, perspective view of the provisional prosthetic system of FIG. 4.

Referring to FIG. 4, another exemplary embodiment of frame component 12 and shell component 14 are depicted as frame component 70 and shell component 72. Frame component 70 and shell component 72 include several components which are identical or substantially identical to components of frame component 12 and shell component 14, respectively, and corresponding reference numerals are used to identify identical or substantially identical components therebetween. As shown in FIG. 4, frame component 70 includes openings 74 formed in condylar bases 28, 30 and anterior bridge portion 32. Similarly, shell component 72 includes projections 76 formed on condylar portions 50, 52 and anterior portion 54. Projections 76 are sized and configured to be received with openings 74 of frame component 70. Thus, as shown in FIG. 5, receipt of projections 76 of shell component 72 within openings 74 of frame component 70 provides a snap-fit connection between frame component 70 and shell component 72.

To separate frame component 70 and shell component 72, a surgeon may exert a force on anterior portion 54 of shell component 72, in a direction away from frame component 70, to disengage one of projections 76 from one of openings 74. Once shell component 72 is removed from frame component 70, a different shell component 72 having different characteristics may be attached to frame component 70 in a similar manner. In another exemplary embodiment, frame component 70 may include a projecting rib and shell component 72 a corresponding groove to facilitate alignment of frame component 70 and shell component 72 to facilitate proper seating and retention of shell component 72 on frame component 70.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A modular provisional system comprising:
a frame component configured to be secured to a distal end of a resected femur to provide a support surface, including a first substantially planar condylar base and a second substantially planar condylar base connected by an anterior bridge portion connecting anterior proximal portions of the first and second condylar bases and configured to abut an anterior femoral resection of the resected femur, and a posterior bridge portion connecting posterior proximal portions of the first and second condylar bases;
wherein the anterior bridge portion including a plurality of engagement structures, the frame component including bone contacting surfaces configured to contact the distal end of the resected femur on three separate planes formed by resected surfaces including a distal resection, the anterior femoral resection and posterior femoral resection; and
a plurality of shell components, each of said plurality of shell components configured to be releaseably secured to said support surface of said frame component by the plurality of engagement structures, said frame component and each of said plurality of shell components cooperable to form different provisional implants each of which replicate the characteristics of at least one nonprovisional component of a prosthesis system, different ones of said plurality of shell components releasably securable to the resected femur via the support surface of the frame component when the frame component is secured to the distal end of the resected femur.

2. The modular provisional system of claim 1, wherein the plurality of engagement structures include an offset rib and each of said plurality of shell components further includes a groove formed therein, said groove of each of said plurality of shell components configured to receive said offset rib to releaseably secure each of said plurality of shell components to said frame component, wherein said offset rib is displaced medially or laterally from a centerline of said anterior bridge portion.

3. The modular provisional system of claim 1, further comprising a plurality of frame components, each of said plurality of frame components configured to be secured to the distal end of the resected femur.

4. The modular provisional system of claim 1, wherein said frame component is metallic and at least one of said plurality of shell components is plastic.

5. The modular provisional system of claim 1, wherein at least one of said plurality of shell components is an injection molded polymer.

6. The modular provisional system of claim 1, wherein at least one of said plurality of shell components further comprises a tapered lead adjacent a frame contacting surface of said at least one shell component of said plurality of shell components to facilitate seating said frame component against said frame contacting surface.

* * * * *